United States Patent [19]

Philippson et al.

[11] 4,118,488
[45] Oct. 3, 1978

[54] 4-ANDROSTEN-3-ONES AND PROCESS FOR THE PREPARATION THEREOF

[75] Inventors: Rainer Philippson, Bergkamen; Bernhard Krieger, Unna; Jorge Casals-Stenzel, Berlin; Ulrich Kerb, Berlin; Wolfgang Losert, Berlin; Klaus Prezewowsky, Berlin; Rudolf Wiechert, Berlin; Dieter Bittler, Berlin, all of Fed. Rep. of Germany

[73] Assignee: Schering Aktiengesellschaft, Berlin, Fed. Rep. of Germany

[21] Appl. No.: 773,982

[22] Filed: Mar. 3, 1977

[30] Foreign Application Priority Data

Mar. 5, 1976 [DE] Fed. Rep. of Germany ....... 2609694
Mar. 5, 1976 [DE] Fed. Rep. of Germany ....... 2609695
Jun. 16, 1976 [DE] Fed. Rep. of Germany ....... 2627187
Jun. 16, 1976 [DE] Fed. Rep. of Germany ....... 2627186
Sep. 30, 1976 [DE] Fed. Rep. of Germany ....... 2644427
Oct. 8, 1976 [DE] Fed. Rep. of Germany ....... 2646043

[51] Int. Cl.² .................... C07J 9/00; A61K 31/56
[52] U.S. Cl. .................... 424/238; 260/397.1; 260/239.5; 260/239.57; 260/397.3; 260/397.5; 424/243
[58] Field of Search .................... 260/397.4, 397.1

[56] References Cited

U.S. PATENT DOCUMENTS

| | | | |
|---|---|---|---|
| 3,137,690 | 6/1964 | Johns | 260/239.55 |
| 3,270,008 | 8/1966 | Dryden et al. | 260/239.55 |
| 3,753,979 | 8/1973 | Arth et al. | 260/239.55 R |
| 3,798,213 | 3/1974 | Arth | 260/239.55 |
| 3,883,512 | 5/1975 | Stache et al. | 260/397.4 |
| 3,966,714 | 6/1976 | Philippson | 260/397.4 |

Primary Examiner—Elbert L. Roberts
Attorney, Agent, or Firm—Millen & White

[57] ABSTRACT

4-Androsten-3-ones of the formula

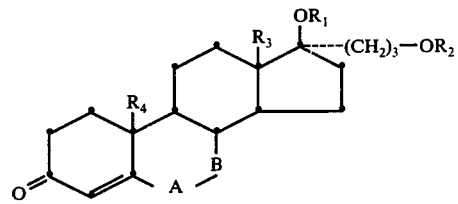

wherein $R_1$ is hydrogen or the acyl radical of an organic or inorganic acid, $R_2$ is hydrogen, alkyl, or the acyl radical of an organic or inorganic acid, $R_3$ is methyl or ethyl, $R_4$ is hydrogen or methyl,

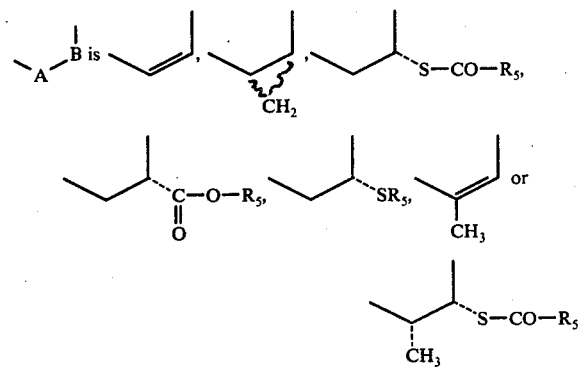

and $R_5$ is lower alkyl, have diuretic activity.

74 Claims, No Drawings

4-ANDROSTEN-3-ONES AND PROCESS FOR THE PREPARATION THEREOF

BACKGROUND OF THE INVENTION

This invention relates to novel 4-androsten-3-ones which have diuretic activity.

SUMMARY OF THE INVENTION

In a compositional aspect, this invention relates to a 4-androsten-3-one of Formula I

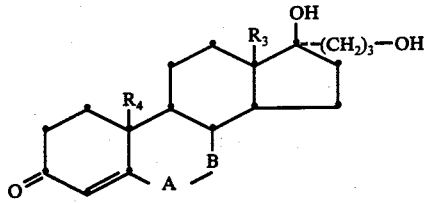

wherein
R$_3$ is methyl or ethyl,
R$_4$ is hydrogen or methyl,

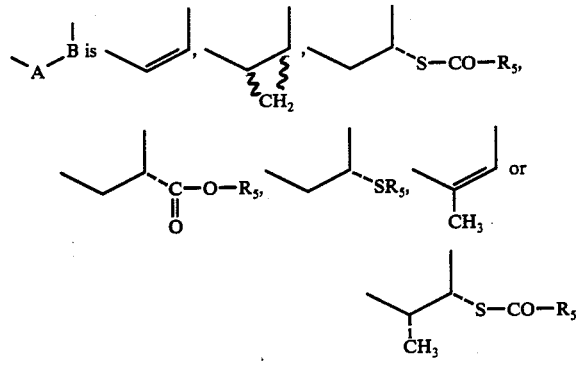

R$_5$ is alkyl or up to 5 carbon atoms, or a physiologically acceptable (a) 17β-hydroxy mono ester thereof, or (b) 17α-(3-hydroxypropyl) mono ester thereof or mono ether thereof, (c) 17β-hydroxy mono ester, 17α-(3-hydroxypropyl) mono ether thereof, or (d) 17β-hydroxy-17α-(3-hydroxypropyl) diester thereof.

In another compositional aspect, this invention relates to a pharmaceutical composition comprising, in unit dosage form, a compound of Formula I, in admixture with a pharmaceutically acceptable carrier.

DETAILED DESCRIPTION

Suitable acid residues are derived from physiologically compatible acids. Examples of inorganic acid residues R$_1$ and R$_2$, respectively, are those derived from nitric acid, sulfuric acid, and phosphoric acid. Particularly preferred organic acid residues R$_2$ and R$_1$, respectively, are those derived from alkanoic acids of 1–8 carbon atoms, preferably 2–8 carbon atoms, for example, monobasic alkanoic acids, such as formic, acetic, propionic, butyric, isobutyric, α-ethylbutyric, pivalic, valeric, isovaleric, α-ethylvaleric, trimethylacetic, 2-methylbutyric, 3-ethylbutyric, caproic, triethylacetic, enanthic, or caprylic acid; cyclic acids, preferably cycloaliphatic acids, such as cyclopropylideneacetic, cyclobutylcarboxylic, cyclopentylcarboxylic, cyclopentylacetic, β-cyclopentylpropionic, cyclohexylcarboxylic, or cyclohexylacetic acid; and also carbocyclic aryl or aralkyl acids, such as benzoic acid, or 2-, 3-, or 4-methylbenzoic acid, and those derived from undecyclic, dodecanoic, tetradecanoic, hexadecanoic, octadecanoic, palmitic, stearic, and β-cyclohexylpropionic acids; 2,3-, 2,4-, 2,6-, 3,4- and 3,5-dimethylbenzoic, ethylbenzoic, naphthoic, 3-methyl-α-naphthoic,β-phenylpropionic, diphenylacetic, and α-naphthylacetic acids.

Since the chemical character of the acyl group is not critical to the activity of compounds of this invention, as long as the acyl group is not toxic and as long as the corresponding acid forms an ester with a primary hydroxy group, residues of other aliphatic and aromatic, unsubstituted and substituted, mono-, di-, and polybasic carboxylic acids, saturated and unsaturated aliphatic, araliphatic, and aromatic carboxylic acids of up to 18 carbon atoms, preferably up to 8 carbon atoms, are contemplated equivalents.

Examples of contemplated equivaltens are acyl derived from dibasic alkanoic acids; for example, oxalic, maleic, fumaric, succinic, malonic, glutaric, α-methylglutaric, β-methylglutaric, β,β-dimethylglutaric, adipic, pimelic, and sebacic acids; dibasic aromatic acids, such as those capable of forming inner anhydrides, e.g. phthalic acid; carbamic acids, such as carbami, phenylcarbamic, n-butylcarbamic, dimethylcarbamic, diethyl-carbamic, and allophanic acids; or heterocyclic acids, such as β-furylcarboxylic, pyrrolecarboxylic, β-pyrrolidinopropionic, N-methylpyrrolidino-2-carboxylic, 6-hydroxy-indolyl-3-acetic, N-methylmorpholino-2-carboxylic, and pyrrole-2-carboxylic acids; or sulfonic acids of 1–8 carbon atoms, preferably 1–12 carbon atoms, such as alkanesulfonic acids, e.g., methane- and ethane- sulfonic acids, and arylsulfonic acids, e.g., benzene- and p-toluenesulfonic acids.

The acyl residues of this invention can also be substituted by one or more substitutents, examples of which are: hydroxy, halo, alkoxy, acyloxy, sulfonyloxy, amido, sulfato, nitro, mercapto, and cyano, for example, acyl residues of glycolic, lactic, citric, tartaric, maleic, glyceric, mannonic, gluconic, and salicyclic acids, or residues of amino acids, e.g., glycine, aminopropionic, diglycolamino, and triglycolamino acids, methylglycine, dimethylglycine, diethylglycine, p-aminosalicyclic, p-aminobenzoic, ethylmercaptoacetic, benzyl-mercaptoacetic, chloroacetic, fluoroacetic, trichloroacetic, trifluoroacetic, thioglycolic, m-nitrobenzoic, 2,3,4-trimethoxybenzoic, phenoxyacetic, and α-naphthyloxyacetic acids.

Especially preferred are residues of dibasic saturated and unsaturated carboxylic acids.

The salts are derived from the corresponding hemiacylates of these dibasic acids. Especially suitable as the cations are the alkali methals, sodium and potassium, and ammonium. Also suitable are divalent alkaline earth metals, such as calcium. In this case there are two molar equivalents of hemiacylate per one molar equivalent of calcium.

Alkyl R$_2$ are saturated, straight-chain and branched-chain alkyl, cyclic alkyl, and aralkyl of up to 20 carbon atoms. Suitable alkyl groups are, for example, methyl, ethyl, butyl, nonyl, undecyl, and stearyl and/or cyclopentyl and cyclohexyl and/or benzyl and triphenylmethyl. Alkyl of up to 10 carbon atoms is preferred.

Lower alkyl R$_5$ are of up to 5 carbon atoms, such as methyl, ethyl, propyl, n-butyl, isobutyl, tert.-butyl, and n-pentyl.

Compounds of Formula I therefore include those wherein:
(a) $R_3$ is methyl;
(b) $R_3$ is ethyl;
(c) $R_4$ is H, including each of (a)–(b);
(d) $R_4$ is methyl, including each of (a)–(b);

(e) 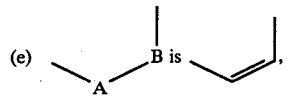

including each of (a)–(d);

(f) 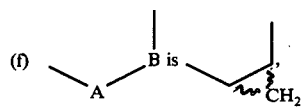

including each of (a)–(d);

(g) 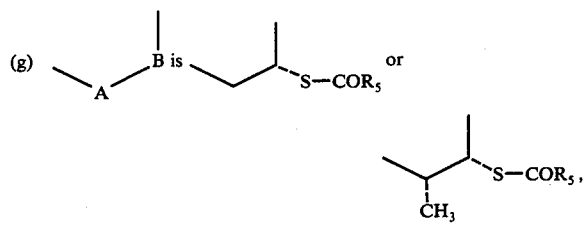

including each of (a)–(d);

(h) 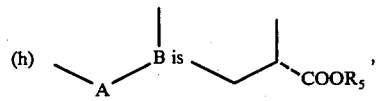

including each of (a)–(d);

(i) 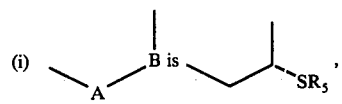

including each of (a)–(d);

(j) 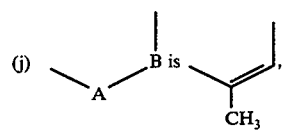

including each of (a)–(d);
(k) 17β-OH is esterified with an acyl radical of an organic or inorganic acid, including each of (a)–(j);
(l) 17α-(3-hydroxypropyl) hydroxyl is esterified with an acyl radical of an organic or inorganic acid, including each of (a)–(k);
(m) 17α-(3-hydroxypropyl) hydroxyl is etherified with an alkyl of up to 20 carbon atoms, including each of (a)–(k);
(n) 17β-OH is present as a free hydroxyl, including each of (a)–(j) and (l)–(m);
(o) 17α-(3-hydroxypropyl) is present as a free hydroxyl, including each of (a)–(k); and
(p) 17β-OH and 17α-(3-hydroxypropyl) each are free OH, including each of (a)–(j).

The compounds produced in accordance with this invention either themselves possess pharmacologically valuable properties or are intermediates for the preparation of medicinal agents having proven activity. For example, 17α-(3-hydroxypropyl)-17β-hydroxy-7α-thioacetyl-4-androsten-3-one is an intermediate for the production of the known aldosterone blocking compound spironolactone, 3-(17β-hydroxy-7α-thioacetyl-3-oxo-4-androsten-17α-yl)-propionic acid lactone.

The compounds of this invention are, inter alia, aldosterone antagonist diuretics, i.e. they reverse the effect of deoxycorticosterone on sodium and potassium excretion. The compounds of this invention, such as 17β-hydroxy-17α-(3-hydroxypropyl)-7α-thioacetyl-4-androsten-3-one, 17β-hydroxy-17α-(3-hydroxypropyl)-7α-ethylthio-4-androsten-3-one, 17β-acetoxy-17α-(acetoxypropyl)-7α-thioacetyl-4-androsten-3-one, 17β-hydroxy-17α-(3-acetoxypropyl)-7α-thioacetyl-6α-methyl-4-androsten-3-one, 17β-hydroxy-17α-(3-hemisuccinyloxy-propyl)-6-methyl-4,6-androstadien-3-one potassium salt, and 17β-hydroxy-17α-(3-hydroxysuccinyloxypropyl)-4,6-androstadien-3-one sodium salt, prove to be surprisingly superior over conventional potassium canrenoate in activity in the Hollmann test model, G. Hollmann et al., "Tubulaere Wirkungen und renale Elimination von Spirolactonen" (Tubular Effects and Renal Elimination of Spirolactones), Naunyn-Schmiedeberg's Arch. Exp. Path. Pharmak. 247 (1964):419; P. Marx, "Renale Wirkungen des d-Aldosterons und seines Antagonisten Spironolacton" (Renal Effects of d-Aldosterone and Its Antagonist Spironolactone), Diss. Med. Fak. FU Berlin 1966.

The invention relates to a process for the preparation of compounds of Formula I or a physiologically acceptable 17β-ester or 17α-(3-propyl ester or ether) thereof

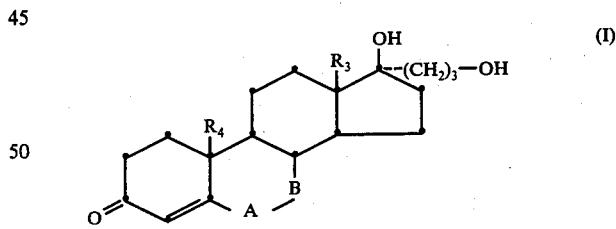

wherein
$R_3$ is methyl or ethyl,
$R_4$ is hydrogen or methyl,

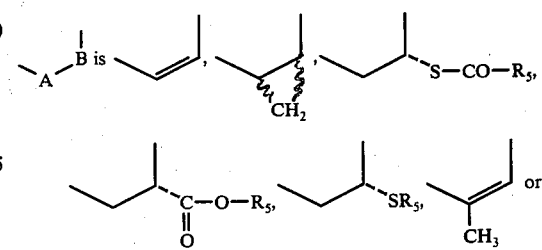

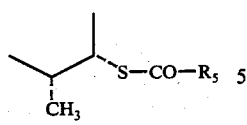

and R₅ is alkyl of up to 5 carbon atoms, wherein
(a) when —A—B— is

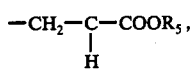

a Δ$^{4,6}$-unsaturated 3-ketoandrostadiene of Formula II

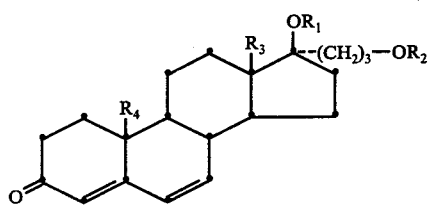

wherein $R_1$ is H or acyl, $R_2$ is H, alkyl or acyl and $R_3$ and $R_4$ are as in Formula I, is blocked at any free hydroxy by an acid-resisting blocking group and treated conventionally with potassium cyanide in a suitable solvent under heating; the thus-produced 3-keto-4,7α-aminomethylidine-5-cyanoandrostane is reacted with heating in an acidic medium to produce a corresponding 3-keto-4α,7α-carbonyl-5-cyanoandrostane, which is heated with an alkali alcoholate;

(b) when —A—B— is

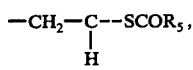

a Δ$^{4,6}$-unsaturated 3-ketoandrostadiene of Formula II is reacted with a thioalkanoic acid in a protonic organic solvent or a mixture thereof, optionally in the presence of a solubilizer;

(c) when —A—B— is

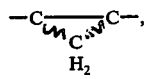

a Δ$^{4,6}$-unsaturated 3-ketoandrostadien of Formula II is treated in a conventional manner with dimethylsulfoxonium methylide in dimethyl sulfoxide as solvent to introduce a methylene group;

(d) when —A—B— is

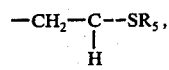

and R₅ is as above, a Δ$^{4,6}$-unsaturated 3-ketoandrostadiene of Formula II is reacted with an alkyl mercaptan in an alkaline solvent;

(e) when —A—B— is

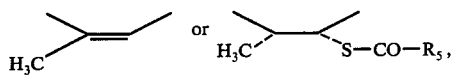

a 4-androsten-3-one of Formula III

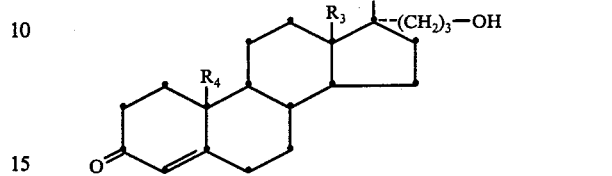

wherein $R_3$ and $R_4$ are as above, is conventionally converted to a Δ$^{3,5}$-compound by enamination or enol ether formation; formaldehyde is added to the Δ$^5$-double bond; water is cleaved from the thus-produced 6-hydroxymethylene compound; the thus-obtained 6-exomethylene steroid is isomerized to a 6-methyl-Δ$^6$-steroid with cyclohexene in the presence of a noble metal catalyst; and, optionally, a thioalkanoic acid is added to the Δ$^6$-double bond; or (f) when $R_1$ and/or $R_2$ are an acyl residue, a 4-androsten-3-one of Formula I in which $R_3$, $R_4$, $R_5$, and —A—B— are as above is conventionally etherified or esterified with an esterification catalyst; a thus-obtained ester is partially saponified, if desired, and optionally esterified with the lastly desired acid and optionally converted to a salt thereof.

A special embodiment of the process of this invention, when $R_2$ is the acyl residue of a dibasic acid, is conversion of a hemiacylate to an ammonium, alkali, or alkaline earth metal salt.

To prepare the compounds of this invention containing an alkoxycarbonyl group in the 7α-position, a Δ$^{4,6}$-unsaturated 3-ketoandrostadiene is suitably dissolved in an appropriate protonic solvent and reacted with an alkali cyanide, such as potassium cyanide. Suitable solvents are alcohols, such as methanol or ethanol, optionally in the presence of a solubilizer, such as ethyl acetate. The use of heat accelerates the reaction which is terminated within a few hours at reflux temperatures. The thus-produced 3-keto-4,7α-(aminomethylidine)-5-cyanoandrostane is extracted and heated in a weakly acidic aqueous solution. In this procedure, the temperature should not exceed 80°–100° C. For acidification purposes, any strongly dissociated acid is suitable, for example, hydrochloric acid, sulfuric acid, or perchloric acid. After cooling, a corresponding 3-keto-4α,7α-carbonyl-5-cyanoandrostane is precipitated which, after separation, is heated with an alkali metal alcoholate, such as sodium ethylate, for example. The alcoholate is produced conveniently directly in the reaction mixture by combining an alkali metal, such as sodium or potassium, with a lower alcohol R₅OH wherein R₅ is as above.

To prepare compounds of this invention containing —S—CO—R₅ in the 7α-position, with R₅ as above, a starting material of Formula II is dissolved in a protonic solvent or in a mixture thereof; a thioalkanoic acid of the formula HS—COR₅ wherein R₅ is as above, is added thereto; and the reaction mixture is heated to temperatures above room temperature up to the boiling temperature of the solvent. Suitable solvents or mixtures thereof are methanol, acetone, and tetrahydrofuran. Optionally utilized solubilizers, such as diisopropyl ether, benzene, and heptane, do not interfere with the course of the reaction.

To produce the compounds of this invention which have methylene in the 6,7-position, a $\Delta^{4,6}$-unsaturated 3-ketoandrostadiene is suitably treated with dimethyl sulfoxonium methylide to indtoduce the methylene group. For this purpose, a $\Delta^{4,6}$-steroid is added, under a protective gase atmosphere, such as nitrogen or argon, gradually either to a suspension of trimethylsulfoxonium iodide with sodium hydride in mineral oil and dimethyl sulfoxide, or to a solution of trimethylsulfoxonium iodide and sodium hydroxide in dimethyl sulfoxide. The reaction is terminated after 10–30 hours at 20°–40° C. The reaction product is extracted and the $6\beta,7\beta$-methylene compound is separated from the $6\alpha,7\alpha$-methylene compound and purified by chromatography.

If it is advantageous to block free hydroxy groups, it is possible to introduce nitryloxy groups, for example, in accordance with the method of DOS (German Unexamined Laid-Open Application) No. 1,618,998.

If the compounds of this invention contain esterified hydroxy groups, for example, blocking groups, provided during the synthesis, the ester bonds can be hydrolyzed by conventional methods. Nitrate ester groups are suitably reduced to the hydroxy group with zinc in acetic solution.

To prepare the compounds of this invention having an alkylthio group in the $7\alpha$-position, a starting material of Formula II is reacted in a suitable solvent with the corresponding alkyl mercaptan. Suitable solvents are particularly organic bases, such as pyridine, piperidine, collidine, and lutidine. The reaction mixture is suitably heated to temperatures above room temperature. Lower temperatures are feasible but lead to undesirably long reaction times, while temperatures up to the boiling point of the reaction mixture can readily be utilized.

In order to produce the compounds of this invention which have a 6-methyl-$\Delta^6$- or a $6\alpha$-methyl-$7\alpha$-alkanoylthio grouping, a 3-keto-$\Delta^4$-grouping is isomerized in compounds of Formula III either by enamination or enol etherification to obtain a 3-enamine or 3-enol ether-$\Delta^{3,5}$-grouping.

For purposes of conducting the enamination, a starting steroid is heated, for example, with pyrrolidine or morpholine in a suitable solvent, such as methanol, methylene chloride, or benzene, optionally with the addition of p-toluenesulfonic acid.

To produce an enol ether, the starting steroid is heated, for example, advantageously with acetone dimehtyl ketal, orthoformic acid ester, or benzyl alcohol in a suitable solvent, such as benzene, dimethylformamide, or dioxane in the presence of p-toluenesulfonic acid or sulfuric acid. Formation of corresponding thioenol ethers with monothioglycol or benzyl mercaptan in pyridine/ethanol is likewise possible.

Formaldehyde is added to a thus-formed 3,5-dienamine or 3-alkoxy-3,5-diene. For this purpose, formaldehyde is gradually added at room temperature to a $\Delta^{3,5}$-steroid dissolved in a suitable solvent. Advantageous solvents are aliphatic alcohols, such as methanol and ethanol, aromatic hydrocarbons, such as benzene and toluene, as well as cycloaliphatic hydrocarbons, such as cyclohexane.

Subsequently, water is cleaved from a thus-formed 6-hydroxymethyl compound. For this purpose, a 6-hydroxymethyl steroid is treated with an acid in a protonic solvent, for example, a combination of dioxane or tetrahydrofuran and hydrochloric acid or p-toluenesulfonic acid and/or methanesulfonic acid chloride in pyridine, optionally while adding lithium bromide with heating.

The thus-obtained 6-exomethylene steroid is then isomerized to a 6-methyl-$\Delta^6$-steroid. For this purpose, the 6-exomethylene steroid is heated, for example, with cyclohexene in the presence of a noble metal catalyst, such as palladium, over a longer period of time. By heating under reflux, the reaction is finished after a few hours. Addition of sodium acetate or potassium acetate shortens the reaction time. The reaction is suitably conducted in a protonic solvent, such as methanol or ehtanol.

If the compound of this invention is to have an alkanoylthio group, a 6-methyl-$\Delta^6$-steroid is reacted with a corresponding thio acid in a protonic solvent, such as methanol or ethanol, optionally with the addition of water. The temperature is not raised excessively above room temperature, but is maintained below the boiling temperature of the solvent.

If a free hydroxy group, such as the primary hydroxy group on the $17\alpha$-propyl residue, is to be etherified, conventional methods can also be employed. The etherification is preferably conducted with the corresponding alkyl halide. Suitable halides are chlorides, bromides, and, preferably, iodides. The hydroxy compound is dissolved, for example, in a polar solvent, and heated in the presence of a base with the alkylating agent to temperatures between room temperature and 100° C. Examples of suitable bases are barium oxide, sodium hydride, potassium carbonate, and alkali alcoholates, such as sodium ethylate. Polar solvents include dimethylformamide; dimethylacetamide; tetrahydrofuran; dioxane; ketones, such as acetone and methyl isobutyl ketone; and alcohols, such as ethanol, butanol, and tert.-butanol.

Esterification of the primary hydroxy group or $17\alpha$-hydroxypropyl group is done by conventional methods. A suitable method is, for example, reaction with an acid anhydride or acid halide in the presence of a tertiary amine, e.g., pyridine, collidine, triethylamine, or 4-dimethylaminopyridine, at room temperature or above. The primary hydroxy group can also be esterified with an acid anhydride using a strong acid, such as p-toluenesulfonic acid as catalyst or with the corresponding acid and trifluoroacetic anhydride at room temperature.

If a free hydroxy group, such as the primary hydroxy group on the $17\alpha$-propyl residue, is to be partially esterified, known methods can also be employed. Especially advantageous is esterification with a heavy metal salt of a corresponding acid, for example, lead acetate or lead ethoxyacetate, in the presence of the corresponding acid anhydride, for example, acetic anhydride and/or ethoxyacetic acid anhydride, at temperatures around room temperature.

To produce the compounds of this invention wherein $R_1$ and/or $R_2$ represent the acyl residue of an organic acid, it is possible to react either a $17\beta$-hydroxy-$17\alpha$-(3-hydroxypropyl)-$\Delta^4$-3-keto steroid already substituted on the B-ring or a $\Delta^{4,6}$-3-keto steroid with an alkanoic acid anhydride. During this process, the primary hydroxy group is first of all esterified and then, only after a prolonged reaction time and/or at an elevated temperature, the tertiary $17\beta$-hydroxy group is esterified. For this purpose, the starting steroid is advantageously dissolved in a basic solvent, such as pyridine, piperidine, triethylamine, collidine, or lutidine, and the corresponding acid anhydride is added thereto. Addition of an esterification catalyst, such as dimethylaminopyridine, is also advantageous.

The primary hydroxy group is esterified after a short period of time, i.e., after 2–5 hours, while esterification of the tertiary hydroxy group requires longer reaction times. Of course, it is possible to accelerate the reaction by heating, for example up to boiling, and in this case the reaction time is shortened to a few hours.

The process of this invention can also be conducted by first esterifying the primary hydroxy group with one acid and thereafter esterifying the tertiary hydroxy group with another acid. The primary hydroxy group can also be esterified simply by heating the 17α-(3-hydroxypropyl)-compound with a corresponding thioalkanoic acid, such as thioacetic acid, thiopropionic acid, or thiobutyric acid.

The process of this invention can also be conducted by first producing a diester, starting a $\Delta^{4,6}$-unsaturated steroid of Formula II ($R_1$ and $R_2$ are H); eliminating the primary acyl group by conventional saponification; and adding a thioalkanoic acid to the structure.

The saponification is suitably effected under mild conditions, such as with methanolic potassium hydroxide solution and cooling.

It is also possible to esterify the primary 23-hydroxy group simultaneously with the introduction of the 7-acylthio group. For this purpose, the reaction is conducted with the desired thio acid with heating without the use of a solvent.

When the primary 23-hydroxy group has been esterified with a dibasic acid, the resulting hemiacylate can be converted to the desired alkali-salt by reaction, for example, with a methanolic potassium or sodium methylate solution. In order to produce the ammonium salt, a solution of ammonia in methanol is advantageously utilized.

The reaction products of this invention are separated by conventional methods, such as precipitation, filtration, or extraction, and are purified, for example, by chromatography and/or recrystallization.

The $\Delta^{4,6}$-unsaturated 3-ketoandrostadiene used as the starting material can be obtained, for example, by first preparing 17β-hydroxy-17α-(3-hydroxypropyl)-4-androstene from 3-keto-4-androsten-17-one in accordance with the process disclosed in DOS No. 2,327,448 and U.S. Pat. No. 3,966,714, and then introducing the $\Delta^6$-double bond, for example, according to the method described by Agnello et al., J. Amer. Soc., 82 (1960):4293.

The starting material 17β-hydroxy-17α-(3-hydroxypropyl)-18-methyl-4,6-estradien-3-one can be prepared as follows:

A suspension of 6.85 g. of potassium tert.-butylate in 32 ml. of absolute tetrahydrofuran is combined with 50 g. of 3-methoxy-18-methyl-1,3,5(10)-estratrien-17-one, C. Rufer et al., Liebigs Ann. Chem. 752:1 (1971). A solution of 1.7 ml. of propargyl alcohol in 3.5 ml. of tetrahydrofuran is added dropwise so that the internal temperature does not rise above 35° C. The mixture is agitated for 3 hours at 35° C. and then acidified with 13 ml. of 20% sulfuric acid to pH 3. The mixture is then stirred for 10 minutes under reflux. The reaction mixture is thereafter added to ice water. The precipitate is filtered off, taken up in ethyl acetate, washed with water, dried, and evaporated, thus obtaining 5.5 g. of 17β-hydroxy-17α-(3-hydroxypropinyl)-3-methoxy-18-methyl-1,3,5(10)-estratriene.

A solution of 5 g. of 17β-hydroxy-17α-(3-hydroxypropinyl)-3-methoxy-18-methyl-1,3,5(10)-estratriene in 50 ml. of tetrahydrofuran is shaken with 500 mg. of Pd/CaCo$_3$ (5%) under hydrogen at room temperature and under normal pressure until hydrogen absorption is terminated. The mixture is then filtered off from the catalyst, and the filtrate evaporated, thus obtaining 4.8 g. of 17β-hydroxy-17α-(3-hydroxypropyl)-3-methoxy-18-methyl-1,3,5,(10)-estratriene.

A solution of 5 g. of 17β-hydroxy-17α-(3-hydroxypropyl)-3-methoxy-18-methyl-1,3,5(10)-estratriene in 200 ml. of absolute tetrahydrofuran is mixed with 450 ml. of liquid ammonia at −60° C. Then, 5 g. of lithium is added in small pieces. The blue solution is stirred for another 2.5 hours at −60° C. and then decomposed by adding ethanol dropwise until decolorization is complete. The ammonia is then evaporated. The residue is taken up in ether, washed with a sodium chloride solution to render the mixture neutral, dried, and evaporated. The residue is dissolved in 150 ml. of methanol and 65 ml. of methylene chloride and heated with 15 ml. of 3N hydrochloric acid for one hour under reflux. After splitting of the enol ether, the solution is concentrated. The residue is taken up in methylene chloride, and the solution is washed neutral with sodium bicarbonate solution, dried, and evaporated, thus obtaining 2 g. of 17β-hydroxy-17α-(3-hydroxypropyl)-18-methyl-4-estren-3-one.

A solution of 2 g. of 17α-(3-hydroxypropyl)-18-methyl-17β-hydroxy-4-estren-3-one, 1.35 g. of chloranil, and 0.03 g. of p-toluenesulfonic acid in 200 ml. of xylene is heated to boiling for one hour. The mixture is then evaporated under vacuum, and the residue is purified by gradient chromatography over $SiO_2$, thus obtaining 140 mg. of 17β-hydroxy-17α-(3-hydroxypropyl)-18-methyl-4,6-estradien-3-one as an amorphous substance. UV: $\epsilon_{285} = 22,000$ (methanol).

The starting compound 17β-hydroxy-17α-(3-hydroxypropyl)-4,6-estradien-3-one can be prepared as follows:

At −60° C., a solution of 10 g. of 17α-(3-hydroxypropyl)-3-methoxy-1,3,5(10)-estratrien-17β-ol (G. E. Arth et al., J. Med. Chem. 6 [1963] : 618) in 400 ml. of absolute tetrahydrofuran is introduced into 900 ml. of liquid ammonia. Then, 10 g. of lithium is added thereto in small pieces and the mixture is agitated for 2.5 hours at −60° C., whereupon the solution is decolorized by the gradual addition of ethanol, and ammonia is allowed to evaporate under agitation. The residue is taken up in ether, washed neutral with a sodium chloride solution, dried, and evaporated. The residue is dissolved in 300 ml. of methanol and 130 ml. of methylene chloride and heated to boiling with 30 ml. of 3N hydrochloric acid for one hour. After concentration of the solution, it is taken up in methylene chloride, washed neutral with sodium bicarbonate solution and water, dried, and evaporated, thus obtaining 7.1 g. of 17α-(3-hydroxypropyl)-17β-hydroxy-4-estren-3-one, m.p. 166°–167° C. (isopropyl ether/methylene chloride).

UV: $\epsilon_{241} = 17,100$ (methanol).

A solution of 4.0 g. of 17α-(3-hydroxypropyl)-17β-hydroxy-4-estren-3-one, 3.3 g. of chloranil, and 0.05 g. of p-toluenesulfonic acid in 400 ml. of xylene is heated to boiling for one hour. Then, the mixture is evaporated under vacuum, and the residue is purified over silica gel by gradient chromatography, thus obtaining 350 mg. of 17β-hydroxy-17α-(3-hydroxypropyl)-4,6-estradien-3-one, m.p. 193°-194.5° C. (acetone/hexane). UV: $\epsilon_{284}$ = 26,900 (methanol).

The pharmacologically active compounds of Formula I can be processed by medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg. in a pharmaceutically acceptable carrier per unit dosage.

The dosage of the compounds according to this invention is 20–500 mg./day when administered to human patients as a diuretic, in the same manner as the know aldosterone antagonist spironolactone.

17α-(3-Hydroxypropyl)-17β-hydroxy-7α-thioacetyl-4-androsten-3-one is especially suitable as an intermediate for the production of the conventional spironolactone. For this purpose, 17α-(3-hydroxypropyl)-17β-hydroxy-7α-thioacetyl-4-androsten-3-one is oxidized by using conventional methods to the spironolactone with chromic acid with lactonization, as in the following example:

0.5 g. of 17α-(3-hydroxypropyl)-17β-hydroxy-7α-thioacetyl-4-androsten-3-one is suspended in 10 ml. of acetone at 0° C. This suspension is combined with Jones reagent by gradually dropping 0.52 ml. of this reagent into the suspension, so that the temperature does not exceed 5° C. The excess Jones reagent is decomposed with methanol. The precipitated chromium salts are filtered off and the filtrate is concentrated to dryness and crystallized by adding methanol. After vacuum filtering and drying, 0.38 g. of 3-(17β-hydroxy-7α-thioacetyl-3-oxo-4-androsten-17α-yl)-propionic acid lactone is obtained, m.p. 202°–205° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

One gram of 17α-(3-hydroxypropyl)-17β-hydroxy-4,6-androstadien-3-one is dissolved in 5 ml. of methanol. Under heating, 0.43 ml. of thioacetic acid is added thereto and then the reaction mixture is maintained under reflux for one hour. Thereafter, the reaction mixture is concentrated to dryness under reduced pressure. The residue is crystallized with acetone. The crystals are vacuum-filtered and dried, thus obtaining 0.75 g. of 17α-(3-hydroxypropyl)-17β-hydroxy-7α-thioacetyl-4-androsten-3-one, m.p. 187°–192° C.

UV: $\epsilon_{239}$ = 18,400.

EXAMPLE 2

(a) 49 ml. of acetic anhydride is cooled to $-10°$ C. and combined dropwise with 29.5 ml. of nitric acid (s.g. = 1.51). With agitation, 10 g. of 17β-hydroxy-17α-(3-hydroxypropyl)-4,6-androstadien-3-one dissolved in 200 ml. of chloroform is gradually added dropwise to the reaction mixture, so that the temperature does not rise above $-5°$ C. The reaction mixture is stirred for 20 minutes at $-5°$ to $-10°$ C. and then poured into ice water.

The chloroform phase is separated. The aqueous phase is extracted with methylene chloride. The combined organic extracts are washed neutral and evaporated under vacuum, thus obtaining 17β-nitryloxy-17α-(3-nitryloxypropyl)-4,6-androstadien-3-one.

(b) 6.5 g. of 17β-nitryloxy-17α-(3-nitryloxypropyl)-4,6-androstadien-3-one is combined in 65 ml. of methanol, 8 ml. of ethyl acetate, and 20 ml. of water with 5 g. of potassium cyanide and heated under reflux for 6 hours. Then the mixture is concentrated under vacuum, the residue is combined with water and neutralized with dilute hydrochloric acid. The thus-precipitated product is vacuum-filtered, washed with water, dried, suspended in methylene chloride, and extracted several times with 6N hydrochloric acid. The hydrochloric acid extract is neutralized under ice cooling with sodium hydroxide. The thus-obtained precipitate is vacuum-filtered, washed with water, and dried. Yield: 3.4 g. of crude 4,7α-(aminomethylidine)-5-cyano-17β-nitryloxy-17α-(3-nitryloxypropyl)-5β-androstan-3-one.

(c) The thus-obtained crude product is heated in 100 ml. of 1N hydrochloric acid for 6 hours under agitation on a steam bath. The reaction mixture is cooled and the thus-formed 4α,7α-carbonyl-5-cyano-17β-nitryloxy-17α-(3-nitryloxypropyl)-5β-androstan-3-one is vacuum-filtered, washed with water, and dried under vacuum.

(d) 2.1 g. of sodium is dissolved in 200 ml. of ethanol; 3 g. of 4α,7α-carbonyl-5-cyano-17β-nitryloxy-17α-(3-nitryloxypropyl)-5β-androstan-3-one is added thereto, and the mixture is heated under reflux for 23 hours. The solution is concentrated under vacuum, poured on ice, and acidified with sulfuric acid. The thus-precipitated product is vacuum-filtered, washed with water, dried, and recrystallized from methanol, thus obtaining 1.7 g. of 17β-nitryloxy-17α-(3-nitryloxypropyl)-3-oxo-4-androstene-7α-carboxylic acid ethyl ester, m.p. 178°–180° C.

(e) To reduce the thus-obtained nitrate ester, 1.6 g. thereof is stirred in 10 ml. of tetrahydrofuran and 10 ml.

of glacial acetic acid with 3.5 g. of zinc dust for 10 minutes at 0°–5° C. The zinc dust is filtered off, the filtrate is concentrated under vacuum and poured into ice water. The thus-precipitated ethyl ester of 17β-hydroxy-17α-(3-hydroxypropyl)-3-oxo-4-androstene-7α-carboxylic acid is vacuum-filtered and recrystallized from acetone-hexane, m.p. 152°–153.5° C.

EXAMPLE 3

Analogously to Example 2(c), 4α,7α-carbonyl-5-cyano-17β-nitrolyoxy-17α-(3-nitryloxypropyl)-5β-androstan-3-one is reacted with sodium methylate to the methyl ester of 17β-nitryloxy-17α-(3-nitryloxypropyl)-3-oxo-4-androstene-7α-carboxylic acid. The blocking groups are removed by reduction, thus obtaining the methyl ester of 17β-hydroxy-17α-(3-hydroxypropyl)-3-oxo-4-androstene-7α-carboxylic acid.

EXAMPLE 4

One gram of 17β-hydroxy-17α-(3-hydroxypropyl)-7α-acetylthio-4-androsten-3-one is combined in 20 ml. of dimethylformamide with 1.2 g. of lead(II) ethoxyacetate and 10 ml. of ethoxyacetic acid anhydride and allowed to stand for 68 hours at room temperature. The mixture is then precipitated into ice water, vacuum-filtered, washed with water, and dried. By recrystallizing twice from acetone-hexane, 790 mg. of 17β-hydroxy-17α-(3-ethoxyacetoxypropyl)-7α-acetylthio-4-androsten-3-one is obtained, m.p. 130°–131° C.

EXAMPLE 5

One gram of 17β-hydroxy-17α-(3-hydroxypropyl)-4,6-androstadien-3-one is heated under reflux with 8 ml. of methanol with 1 ml. of thiopropionic acid for 1.5 hours. The mixture is then evaporated under vacuum, and the residue is recrystallized from acetone-hexane, thus obtaining 17β-hydroxy-17α-(3-hydroxypropyl)-7α-propionylthio-4-androsten-3-one, m.p. 165°–167° C.

EXAMPLE 6

1.8 g. of trimethylsulfoxonium iodide and 2.8 g. of sodium hydroxide are stirred in 32 ml. of dimethyl sulfoxide for 15 minutes under argon gas. Thereafter 1 g. of 17β-hydroxy-17α-(3-hydroxypropyl)-4,6-androstadien-3-one is introduced into the reaction mixture and the latter agitated under argon for another 24 hours at 35° C. The mixture is then poured into acetic ice water. The thus-precipitated product is vacuum-filtered and dissolved in methylene chloride. The methylene chloride extract is washed with water, dried over sodium sulfate, and evaporated under vacuum. The residue is purified by thin layer chromatography in the system chloroform-methanol (9:1). Recrystallization from acetone yields 530 mg. of 17β-hydroxy-17α-(3-hydroxypropyl)-6β,7β-methylene-4-androsten-3-one, m.p. 170°–172° C.

UV: $\epsilon_{263} = 18,300$.

EXAMPLE 7

One gram of 17β-nitryloxy-17α-(3-nitryloxypropyl)-4,6-androstadien-3-one is refluxed for 1.5 hours in 10 ml. of methanol and 2 ml. of thioacetic acid. The mixture is then concentrated by evaporation under vacuum and the residue is recrystallized from acetone-hexane, thus obtaining 850 mg. of 7α-acetylthio-17β-nitryloxy-17α-(3-nitryloxypropyl)-4-androsten-3-one, m.p. 178°–179° C.

EXAMPLE 8

A solution of 1 g. of 17β-hydroxy-17α-(3-hydroxypropyl)-18-methyl-4,6-estradien-3-one in 5 ml. of methanol is heated with 1 ml. of thioacetic acid for ½ hour on a steam bath. The reaction mixture is concentrated under nitrogen and the residue taken up in ethyl acetate. The solution is washed with bicarbonate solution and water and concentrated by evaporation, thus obtaining 0.35 g. of 7α-acetylthio-17β-hydroxy-17α-(3-hydroxypropyl)-18-methyl-4-estren-3-one, m.p. 188°–190° C. (methanol).

UV: $\epsilon_{238} = 19,900$ (methanol).

EXAMPLE 9

In accordance with Example 8, by reacting 17β-hydroxy-17α-(3-hydroxypropyl)-18-methyl-4,6-estradien-3-one with thiopropionic acid, 17β-hydroxy-17α-(3-hydroxypropyl)-18-methyl-7α-propionylthio-4-estren-3-one is obtained, m.p. 179°–188° C. (methanol).

EXAMPLE 10

A solution of 3 g. (13.8 millimoles) of trimethylsulfoxonium iodide in 60 ml. of absolute dimethyl sulfoxide is combined with 330 mg. (13.8 millimoles) of sodium hydride as a 50% mineral oil suspension. The solution is agitated under nitrogen at room temperature until the evolution of hydrogen has ceased. Thereafter, 3 g. (0.87 millimole) of 17β-hydroxy-17α-(3-hydroxypropyl)-18-methyl-4,6-estradien-3-one is added thereto and the mixture is agitated under nitrogen at room temperature until the starting material can no longer be detected by thin-layer chromatography. The reaction mixture is worked up by introducing the mixture into acetic ice water and extraction with ethyl acetate. After the solvent has been removed by evaporation, the residue is purified by gradient chromatography on silica gel. First of all, 790 mg. of 17β-hydroxy-17α-(3-hydroxypropyl)-18-methyl-6α,7α-methylene-4-estren-3-one is eluted and then follows 180 mg. of 17β-hydroxy-17α-(3-hydroxypropyl)-18-methyl-6β,7β-methylene-4-estren-3-one.

EXAMPLE 11

A solution of 400 mg. of 7α-acetylthio-17β-hydroxy-17α-(3-hydroxypropyl)-18-methyl-4-estren-3-one in 3 ml. of pyridine is combined with 200 mg. of propionyloxyacetyl chloride and allowed to stand for 24 hours at room temperature. The reaction mixture is then introduced into ice water and the precipitate is filtered off. The residue is dissolved in methylene chloride, washed, dried, and evaporated, thus obtaining 320 mg. of 7α-acetylthio-17β-hydroxy-18-methyl-17α-(3-propionyloxyacetoxypropyl)-4-estren-3-one.

EXAMPLE 12

A solution of 800 mg. of 17β-hydroxy-17α-(3-hydroxypropyl)-18-methyl-6β, 7β-methylene-4-estren-3-one in 5 ml. of pyridine is combined with 400 mg. of acetoxyacetic acid chloride; the mixture is allowed to stand for 20 hours at room temperature. Then, the reaction mixture is introduced into ice water and worked up as described in Example 11, thus producing 730 mg. of 17β-hydroxy-17α-(3-acetoxyacetyloxypropyl)-18-methyl-6β,7β-methylene-4-estren-3-one.

EXAMPLE 13

250 mg. of 7α-acetylthio-17β-hydroxy-17α-(3-hydroxypropyl)-18-methyl-4-estren-3-one is dissolved in 2 ml. of pyridine. 1 ml. of acetic anhydride is added thereto and the mixture is allowed to stand for 20 hours at room temperature. Thereafter, the mixture is precipitated into ice water, the substance is taken up in methylene chloride, and the solution is washed, dried, and evaporated, thus obtaining 180 mg. of 7α-acetylthio-17β-hydroxy-17α-(3-acetoxypropyl)-18-methyl-4-estren-3-one.

EXAMPLE 14

As described in Example 13, 17β-hydroxy-17α-(3-hydroxypropyl)-18-methyl-6β,7β-methylene-4-estren-3-one is reacted with acetic anhydride to yield 17β-hydroxy-17α-(3-acetoxypropyl)-18-methyl-6β,7β-methylene-4-estren-3-one.

EXAMPLE 15

A solution of 5 g. of 7α-acetylthio-17β-hydroxy-17α-(3-hydroxypropyl)-18-methyl-4-estren-3-one in 50 ml. of absolute dimethylformamide is combined with 15 ml. of methyl iodide and 18 g. of pulverized barium oxide. Under vigorous agitation, the reaction is allowed to take place at about 40° C. After 6 hours, the reaction mixture is taken up in methylene chloride and filtered off from the residue. The organic phase is washed, dried, and evaporated. The residue is purified by gradient chromatography, thus obtaining 2.3 g. of 7α-acetylthio-17β-hydroxy-17α-(3-methoxypropyl)-18-methyl-4-estren-3-one.

EXAMPLE 16

A solution of 1.4 g. of triphenylchloromethane in 5 ml. of absolute pyridine is combined with 1.62 g. of 7α-acetylthio-17β-hydroxy-17α-(3-hydroxypropyl)-18-methyl-4-estren-3-one and allowed to stand for 3 days at room temperature. The reaction mixture is then introduced into ice water, the precipitate is filtered off and washed neutral with water. The residue is purified by gradient chromatography, thus obtaining 1.25 g. of 7α-acetylthio-17β-hydroxy-18-methyl-17α-(3-triphenylmethoxypropyl)-4-estren-3-one.

EXAMPLE 17

A solution of 1 g. of 17β-hydroxy-17α-(3-hydroxypropyl)-4,6-estradien-3-one is heated on a steam bath under nitrogen in 5 ml. of methanol with 1 ml. of thioacetic acid for ½ hour. The reaction mixture is evaporated under nitrogen, and the residue is taken up in ethyl acetate. The solution is washed with bicarbonate solution and water and evaporated, thus obtaining 0.4 g. of 7α-acetylthio-17β-hydroxy-17α-(3-hydroxypropyl)-4-estren-3-one, m.p. 177°–179° C. (acetone-hexane).

UV: $\epsilon_{238} = 19,000$ (methanol).

EXAMPLE 18

In accordance with Example 17, 17β-hydroxy-17α-(3-hydroxypropyl)-4,6-estradien-3-one and thiopropionic acid yield 17β-hydroxy-17α-(3-hydroxypropyl)-7α-propionylthio-4-estren-3-one, m.p. 164°–175° C. (acetone-hexane).

UV: $\epsilon_{237} = 18,800$ (methanol).

EXAMPLE 19

A solution of 2 g. (9.2 millimoles) of trimethylsulfoxonium iodide in 40 ml. of absolute dimethyl sulfoxide is combined with 220 mg. (9.2 millimoles) of sodium hydride as a 50% mineral oil suspension. The solution is stirred at room temperature under nitrogen until the evolution of hydrogen ceases. Thereafter, 2 g. (7 millimoles) of 17β-hydroxy-17α-(3-hydroxypropyl)-4,6-estradien-3-one is added thereto and the reaction mixture is agitated under nitrogen until the starting material can no longer be detected by thin-layer chromatography. For purposes of working up the reaction mixture, the latter is introduced into acetic ice water and extracted with ethyl acetate. After the solvent has been evaporated, the residue is purified by gradient chromatography on silica gel. First of all, 850 mg. of 17β-hydroxy-17α-(3-hydroxypropyl)-6α,7α-methylene-4-estren-3-one is isolated and thereafter the desired 17β-hydroxy-17α-(3-hydroxypropyl)-6β, 7β-methylene-4-estren-3-one is obtained (190 mg.).

EXAMPLE 20

A solution of 800 mg. of 7α-acetylthio-17β-hydroxy-17α-(3-hydroxypropyl)-4-estren-3-one in 5 ml. of pyridine is combined with 400 mg. of propionyloxyacetyl chloride and allowed to stand for 24 hours at room temperature. The reaction mixture is then introduced into ice water and the precipitate is filtered off. The precipitate is dissolved in methylene chloride, washed, dried, and evaporated, thus producing 650 mg. of 7α-acetylthio-17β-hydroxy-17α-(3-propionyloxyacetyloxypropyl)-4-estren-3-one.

EXAMPLE 21

A solution of 850 mg. of 17β-hydroxy-17α-(3-hydroxypropyl)-6β,7β-methylene-4-estren-3-one in 5 ml. of pyridine is combined with 450 mg. of acetoxyacetic acid chloride. The reaction mixture is allowed to stand for 20 hours at room temperature. The mixture is then introduced into ice water and worked up as described in Example 20, thus obtaining 530 mg. of 17β-hydroxy-17α-(3-acetoxyacetyloxypropyl)-6β,7β-methylene-4-estren-3-one.

EXAMPLE 22

500 mg. of 7α-acetylthio-17β-hydroxy-17α-(3-hydroxypropyl)-4-estren-3-one is dissolved in 2 ml. of pyridine, 1 ml. of acetic anhydride is added thereto, and the mixture is allowed to stand for 20 hours at room temperature. Thereafter, the reaction mixture is precipitated into ice water and the precipitate taken up in methylene chloride. The solution is washed, dried, and evaporated, thus obtaining 375 mg. of 7α-acetylthio-17β-hydroxy-17α-(3-acetoxypropyl)-4-estren-3-one, m.p. 77°–80° C. (pentane-isopropyl ether).

UV: $\epsilon_{237} = 19,000$ (methanol).

EXAMPLE 23

As described in Example 22, 17β-hydroxy-17α-(3-hydroxypropyl)-6β,7β-methylene-4-estren-3-one is reacted with acetic anhydride to obtain 17β-hydroxy-17α-(3-acetoxypropyl)-6β,7β-methylene-4-estren-3-one.

EXAMPLE 24

A solution of 500 mg. of 7α-acetylthio-17β-hydroxy-17α-(3-hydroxypropyl)-4-estren-3-one in 5 ml. of absolute dimethylformamide is combined with 1.5 ml. of methyl iodide and 1.8 g. of pulverized barium oxide. Under vigorous agitation, the temperature is allowed to rise gradually to 40° C. under cooling. After 6 hours, the reaction mixture is taken up in methylene chloride and filtered off from the residue. The organic phase is washed, dried, and evaporated. The residue is purified by gradient chromatography, thus obtaining 270 mg. of 7α-acetylthio-17β-hydroxy-17α-(3-methoxypropyl)-4-estren-3-one.

EXAMPLE 25

A solution of 2.8 g. (10 millimoles) of triphenylchloromethane in 10 ml. of absolute pyridine is combined with 3.2 g. (8 millimoles) of 7α-acetylthio-17β-hydroxy-17α-(3-hydroxypropyl)-4-estren-3-one and the mixture is allowed to stand for 3 days at room temperature. The reaction mixture is then poured into ice water; the precipitate is filtered off and washed neutral with water. The residue is purified by gradient chromatography, thus obtaining 2.5 g. of 7α-acetylthio-17β-hydroxy-17α-(3-triphenylmethoxypropyl)-4-estren-3-one.

EXAMPLE 26

1.5 g. of 7α-acetylthio-17β-hydroxy-17α-(3-hydroxypropyl)-4-estren-3-one is dissolved in 5 ml. of pyridine and heated to boiling for 3 hours under argon with 0.75 g. of succinic anhydride. The mixture is allowed to stand overnight at room temperature, then poured into sulfuric ice water and extracted with ethyl acetate. The ethyl acetate extract is washed neutral with saturated sodium chloride solution, dried, and evaporated. The residue, 7α-acetylthio-17β-hydroxy-17α-(3-hydroxysuccinyloxypropyl)-4-estren-3-one, is obtained in the form of an amorphous compound.

UV: $\epsilon_{238} = 19,500$ (methanol).

EXAMPLE 27

500 mg. of the hemisuccinate produced in accordance with Example 26 is dissolved in 15 ml. of absolute methanol. The solution is brought to pH 8 with 0.1N potassium methylate solution (5.5 ml.), concentrated under vacuum, and precipitated into 200 ml. of ether. The thus-precipitated potassium salt is filtered off, dissolved in methanol, and purified by repeated reprecipitation in ether, thus obtaining 190 mg. of amorphous 7α-acetylthio-17β-hydroxy-17α-(3-hydroxysuccinyloxypropyl)-4-estren-3-one as the potassium salt.

UV: $\epsilon_{239} = 18,900$ (methanol).

EXAMPLE 28

One gram of 17β-hydroxy-17α-(3-hydroxypropyl)-4,6-androstadien-3-one in 20 ml. of pyridine and 20 ml. of ethyl mercaptan is agitated in a glass autoclave for 20 hours at 50° C. After cooling, 4 ml. of triethylamine is added to the reaction mixture and the latter is stirred for another 25 hours at 50° C. Thereafter, the mixture is poured into ice-cold, saturated sodium chloride solution. The thus-precipitated product is vacuum-filtered and recrystallized from acetone-hexane. The thus-produced 7α-ethylthio-17β-hydroxy-17α-(3-hydroxypropyl)-4-androsten-3-one melts at 205°–207° C.

EXAMPLE 29

0.5 g. of 17β-hydroxy-17α-(3-hydroxypropyl)-4,6-androstadien-3-one is agitated under boiling in 10 ml. of piperidine and 10 ml. of butyl mercaptan in a glass autoclave for 5 hours and then allowed to stand at room temperature for 42 hours. Thereafter, the reaction mixture is concentrated under vacuum and the residue is crystallized with acetone-hexane, thus producing 17β-hydroxy-17α-(3-hydroxypropyl)-7α-butylthio-4-androsten-3-one, which melts at 196°–205° C. with decomposition.

EXAMPLE 30

A solution of 0.75 g. of 17β-hydroxy-17α-(3-hydroxy-propyl)-4,6-estradien-3-one in 15 ml. of piperidine and 15 ml. of ethyl mercaptan is agitated in a glass autoclave under argon for 5 hours at 50° C. and then allowed to stand at room temperature for 50 hours. The mixture is then concentrated under vacuum. The residue is recrystallized from acetone-hexane, and the product is 17β-hydroxy-17α-(3-hydroxypropyl)-7α-ethylthio-4-estren-3-one as an amorphous compound.

EXAMPLE 31

In accordance with Example 30, 0.8 g. of 17β-hydroxy-17α-(3-hydroxypropyl)-18-methyl-4,6-estradien-3-one is reacted to 17β-hydroxy-17α-(3-hydroxypropyl)-7α-ethylthio-18-methyl-4-estren-3-one, which is obtained as an amorphous compound.

EXAMPLE 32

15.0 g. of 17β-hydroxy-17α-(3-hydroxypropyl)-4-androsten-3-one is refluxed in 75 ml. of methanol and 7.5 ml. of pyrrolidine for 15 minutes. The mixture is then cooled in an ice bath. The thus-crystallized precipitate is vacuum-filtered and washed with a small amount of ice-cold methanol, thus obtaining 12.0 g. of 17α-(3-hydroxypropyl)-3-pyrrolidino-3,5-androstadien-17β-ol.

UV: $\epsilon_{276} = 21,300$.

11.5 g. of 17α-(3-hydroxypropyl)-3-pyrrolidino-3,5-androstadien-17β-ol is dissolved in 794 ml. of ethanol and 397 ml. of benzene. Then, 20.8 ml. of 40% formaldehyde solution is added dropwise to the reaction mixture and the latter is stirred for one hour at room temperature. The mixture is thereafter exhaustively concentrated under vacuum and the residue is chromatographed on silica gel, thus obtaining 5.25 g. of 17β-hydroxy-6β-hydroxymethyl-17α-(3-hydroxypropyl)-4-androsten-3-one.

UV: $\epsilon_{241} = 11,100$.

5.25 g. of 17β-hydroxy-6β-hydroxymethyl-17α-(3-hydroxypropyl)-4-androsten-3-one is stirred in 260 ml. of dioxane with 15.2 ml. of 5N hydrochloric acid for 2.5 hours at room temperature. The reaction solution is then combined with excess sodium bicarbonate and filtered from the undissolved residue. The filtrate is evaporated to dryness under vacuum. The residue is chromatographed on silica gel, thus obtaining 3.8 g. of 17β-hydroxy-17α-(3-hydroxypropyl)-6-methylene-4-androsten-3-one. A sample recrystallized from acetone melts at 178°–179.5° C.

UV: $\epsilon_{261} = 11,000$.

3.5 g. of 17β-hydroxy-17α-(3-hydroxypropyl)-6-methylene-4-androsten-3-one is combined in 122 ml. of ethanol with 1.75 g. of anhydrous sodium acetate and 257 mg. of palladium on carbon, (5%), and, at the boiling point, 0.7 ml. of cyclohexane in 20 ml. of ethanol is added in incremental portions over a period of 8 hours. The mixture is then filtered off from the catalyst and the filtrate extensively concentrated under vacuum. The residue is taken up in methylene chloride, washed with water, dried, evaporated, and chromatographed on silica gel, thus obtaining 1.9 g. of 17β-hydroxy-17α-(3-hydroxypropyl)-6-methyl-4,6-androstadien-3-one. A sample recrystallized from diisopropyl ether-acetone melts at 197°–202° C.

UV: $\epsilon_{291} = 21,100$.

EXAMPLE 33

500 mg. of 17β-hydroxy-17α-(3-hydroxypropyl)-6-methyl-4,6-androstadien-3-one is stirred in 5 ml. of thioacetic acid for 6.5 hours at 100° C. The mixture is then diluted with ether, washed with water and saturated sodium bicarbonate solution, dried, and evaporated. The residue is purified by way of preparative layer chromatography, thus obtaining 330 mg. of 7α-acetylthio-17α-(3-acetoxypropyl)-17β-hydroxy-6α-methyl-4-androsten-3-one as an oil.

UV: $\epsilon_{238} = 19,200$.

EXAMPLE 34

1.0 g. of 17β-hydroxy-17α-(3-hydroxypropyl)-6-methyl-4,6-androstadien-3-one is combined in 10 ml. of methanol with 2 ml. of water and 2 ml. of thioacetic acid and stirred for 18 hours at 50° C. The mixture is then diluted with ether, washed with water and saturated sodium bicarbonate solution, dried, and concentrated by evaporation. After chromatography on silica gel, the product is recrystallized from diisopropyl ether-acetone, thus obtaining 650 mg. of 7α-acetylthio-17β-hydroxy-17α-(3-hydroxypropyl)-6α-methyl-4-androsten-3-one, m.p. 175°-175.5° C.

UV: $\epsilon_{239} = 18,500$.

EXAMPLE 35

250 mg. of 7α-acetylthio-17β-hydroxy-17α-(3-hydroxypropyl)-6α-methyl-4-androsten-3-one is allowed to stand in 1 ml. of pyridine with 0.5 ml. of butyric anhydride for 24 hours at room temperature. After precipitation into ice water, the thus-separated oil is filtered off, taken up in ether, washed with water, and dried. The residue obtained after evaporation is purified by way of preparative layer chromatography, thus producing 210 mg. of 7α-acetylthio-17α-(3-butyryloxypropyl)-17β-hydroxy-6α-methyl-4-androsten-3-one as an oil.

UV: $\epsilon_{239} = 18,600$.

EXAMPLE 36

400 mg. of 17β-hydroxy-17α-(3-hydroxypropyl)-6-methyl-4,6-androstadien-3-one is agitated in 4 ml. of methanol with 0.8 ml. of water and 0.8 ml. of thiopropionic acid for 48 hours at 50° C. The mixture is worked up as described in Example 34 and purified by way of preparative layer chromatography, thus obtaining 210 mg. of 17β-hydroxy-17α-(3-hydroxypropyl)-6α-methyl-7α-propionylthio-4-androsten-3-one.

UV: $\epsilon_{239} = 18,200$.

EXAMPLE 37

350 mg. of 17β-hydroxy-17α-(3-hydroxypropyl)-6-methyl-4,6-androstadien-3-one is heated under reflux in 3.5 ml. of pyridine with 350 mg. of succinic anhydride for one hour. The mixture is then stirred into ice water, the thus-separated oil is filtered off, taken up in methylene chloride, dried, and evaporated. The residue is chromatographed on silica gel, thus producing 420 mg. of 17β-hydroxy-6-methyl-17α-(3-hemi-succinyloxypropyl)-4,6-androstadien-3-one (amorphous).

UV: $\epsilon_{291} = 20,500$.

EXAMPLE 38

420 mg. of 17β-hydroxy-6-methyl-17α-(3-hemi-succinyloxypropyl)-4,6-androstadien-3-one is dissolved in 20 ml. of absolute methanol and reacted with 6.4 ml. of methanolic 0.1N potassium methylate solution to the point of equivalency. The reaction solution is then precipitated into absolute ether. The precipitate is vacuum-filtered, washed with ether, and dried, thus producing 340 mg. of 17β-hydroxy-6-methyl-17α-(3-hemisuccinyloxypropyl)-4,6-androstadien-3-one potassium salt (amorphous), m.p. 130° C. (with decomposition).

UV: $\epsilon_{291} = 21,300$.

EXAMPLE 39

350 mg. of 17β-hydroxy-6-methyl-17α-(3-hemi-succinyloxypropyl)-4,6-androstadien-3-one is reacted as described in Example 38 with methanolic sodium methylate solution and then worked up, thus producing 310 mg. of 17β-hydroxy-6-methyl-17α-(3-hemisuccinyloxypropyl)-4,6-androstadien-3-one sodium salt.

UV: $\epsilon_{291} = 21,000$.

EXAMPLE 40

As described in Example 37, by reacting 17β-hydroxy-17α-(3-hydroxypropyl)-18-methyl-4,6-estradien-3-one with succinic anhydride in pyridine, 17β-hydroxy-17α-(3-hydroxy-succinyloxypropyl)-18-methyl-4,6-estradien-3-one is obtained as an amorphous compound.

UV: $\epsilon_{284} = 24,100$ (methanol).

EXAMPLE 41

As described in Example 38, 17β-hydroxy-17α-(3-hydroxysuccinyloxypropyl)-18-methyl-4,6-estradien-3-one yields the potassium salt as an amorphous compound.

UV: $\epsilon_{285} = 22,900$ (methanol).

EXAMPLE 42

10 g. of 7α-acetylthio-17β-hydroxy-17α-(3-hydroxypropyl)-4-androsten-3-one is dissolved in 50 ml. of pyridine; 4.5 g. of succinic anhydride is added thereto and the mixture is heated to boiling for 30 minutes under argon gas. After cooling, the mixture is stirred into sulfuric ice water. The thus-precipitated product is vacuum-filtered, washed neutral, and dried. By recrystallization from methylene chloride/methanol, 10.4 g. of 7α-acetylthio-17β-hydroxy-17α-(3-hydroxysuccinyloxypropyl)-4-androsten-3-one is obtained, m.p. 201°-203° C. (decomposition), is obtained.

EXAMPLE 43

1.1 g. of the hemisuccinate produced in the foregoing example is dissolved in 150 ml. of absolute methanol and adjusted to pH 8 with 0.1N potassium methylate solution in methanol. The solution is concentrated under vacuum, the concentrate is precipitated into ether, and the potassium salt is vacuum-filtered. After repeated reprecipitation, 850 mg. of 7αacetylthio-17β-hydroxy-17 α -(3-hydroxysuccinyloxypropyl)-4-androsten-3-one potassium salt, decomposition point 150° C., is obtained.

EXAMPLE 44

One gram of 7 α-acetylthio-17 βhydroxy-17 α-(3-hydroxypropyl)-4-androsten-3-one is stirred for 72 hours at room temperature in 4 ml. of pyridine, 10 ml. of dimethyl-formamide, 2 ml. of acetic anhydride, and 100 mg. of 4-dimethylaminopyridine. The mixture is precipitated into ice water, vacuum-filtered, washed with water, and dried. By recrystallization from ether-pentane, 17β-acetoxy-17α-(3-acetoxypropyl)-7α-acetylthio-4-androsten-3-one, m.p. 110°–112° C., is obtained.

EXAMPLE 45

0.64 g. of 17α-(3-propionyloxypropyl)-17β-hydroxy-7α-propionylthio-4-androsten-3-one, prepared from 2 g. of 17β-hydroxy-17α-(3-hydroxypropyl)-4,6-androstadien-3-one in 5.4 ml. of thiopropionic acid under agitation and heating to 90° C. under argon gas for a period of 4 hours, evaporation under vacuum and chromatographing of the residue on silica gel, and then eluting 1.89 g. of oily 17α-(3-propionyloxypropyl)-17β-hydroxy-7α-propionylthio-4-androsten-3-one with hexane-ethyl acetate, 1:1; UV: $\epsilon_{239}$ = 17,200, is dissolved in 2.5 ml. of pyridine, combined with 1.25 ml. of acetic anhydride and 60 mg. of 4-dimethylaminopyridine and agitated for 67 hours at room temperature. The mixture is combined with ice water and extracted with methylene chloride. The solution is washed with 1N sulfuric acid and water, and evaporated under vacuum. After purifying the residue by layer chromatography, 17α-(3-propionyloxypropyl)-17β-acetoxy-7α-propionylthio-4-androsten-3-one is obtained.

UV: $\epsilon_{238}$ = 17,800 (methanol).

EXAMPLE 46

17β-Hydroxy-17α-(3-acetoxypropyl)-7α-acetylthio-4-androsten-3-one is acetylated analogously to Example 45. This starting compound is prepared as follows: 2 g. of 17α-(3-hydroxypropyl)-17β-hydroxy-4,6-androstadien-3-one is heated in 1.8 ml. of thioacetic acid for 30 minutes at 90° C. Thereafter, the excess thioacetic acid is removed by distillation under reduced pressure, and the residue is chromatographed, thus obtaining 1.1 g. of 17β-hydroxy-17α-(3-acetoxypropyl)-7α-acetylthio-4-androsten-3-one, m.p. 135°–140° C. (decomposition). The final product is 17β-acetoxy-17α-(3-acetoxypropyl)-7α-acetylthio-4-androsten-3-one which is identical to the compound prepared in accordance with Example 44.

EXAMPLE 47

150 mg. of 17β-hydroxy-17α-(3-hydroxypropyl)-6β,7β-methylene-4-androsten-3-one is heated under reflux for 8 hours in 2 ml. of pyridine and 1 ml. of acetic anhydride under argon gas. After the reaction mixture has been worked up as described in Example 45, 17β-acetoxy-17α-(3-acetoxypropyl)-6β,7β-methylene-4-androsten-3-one is obtained.

EXAMPLE 48

300 mg. of 17β-hydroxy-17α-(3-hydroxypropyl)-4,6-estradien-3-one is heated to boiling in 2 ml. of pyridine and 1 ml. of acetic anhydride for 24 hours under a protective gas. After the reaction mixture has been worked up and purified by chromatography, 140 mg. of 17β-acetoxy-17α-(3-acetoxypropyl)-4,6-estradien-3-one is obtained. 100 mg. of the thus-produced 17β-acetoxy-17α-(3-acetoxypropyl)-4,6-estradien-3-one is dissolved in 1 ml. of methanol and refluxed for one hour with 0.5 ml. of thioacetic acid. After evaporation and purification by chromatography, 17β-acetoxy-17α-(3-acetoxypropyl)-7α-acetylthio-4-estren-3-one is produced.

EXAMPLE 49

500 mg. of 17β-hydroxy-17α-(3-hydroxypropyl)-4,6-estradien-3-one is heated in 2 ml. of thiopropionic acid under agitation and argon gas for 4 hours to 90° C. Thereafter, the mixture is evaporated under vacuum and the residue chromatographed on silica gel. With hexane-acetone 2:1, 120 mg. of 17α-(3-propionyloxypropyl)-17β-hydroxy-7α-propionylthio-4-estren-3-one which is reacted analogously to Example 45 with 1.2 ml. of acetic anhydride in 2.4 ml. of pyridine in the presence of 50 mg. of 4-dimethylaminopyridine for a period of 67 hours at room temperature and then worked up. After purification by layer chromatography, 17α-(3-propionyloxypropyl)-17β-acetoxy-7α-propionylthio-4-estren-3-one is obtained.

EXAMPLE 50

100 mg. of 17β-hydroxy-17α-(3-hydroxypropyl)-7α-thioacetyl-4-androsten-3-one is stirred in 2 ml. of pyridine with 2 ml. of undecylic acid anhydride with the addition of 30 mg. of dimethylaminopyridine for 7 hours at 50° C. Thereafter, the reaction mixture is poured into ice water, extracted with pentane and vacuum-filtered. The residue is extracted with methylene chloride, washed with 1N hydrochloric acid and water, and the residue is concentrated, thus producing 17β-hydroxy-17α-(3-undecyloxypropyl)-7α-thioacetyl-4-androsten-3-one as an oil.

EXAMPLE 51

10 g. of 17β-hydroxy-17α-(3-hydroxypropyl)-4,6-androstadien-3-one is heated to boiling for 24 hours under argon gas in 40 ml. of pyridine and 20 ml. of acetic anhydride. After the reaction mixture has been worked up and chromatographed 17β-acetoxy-17α-(3-acetoxypropyl)-4,6-androstadien-3-one is obtained, m.p. 84°–85° C. Three grams of the thus-obtained diacetate is dissolved in 12 ml. of methanol and 12 ml. of methylene chloride, cooled to 0° C., and combined with a solution of 0.18 g. of potassium hydroxide in 6 ml. of methanol. The mixture is stirred under argon for 10 hours at 20° C., neutralized with acetic acid, and evaporated under vacuum. The residue is dissolved in methylene chloride, washed with water, and evaporated. After stirring the mixture with isopropyl ether, 2.6 g. of amorphous 17β-acetoxy-17α-(3-hydroxypropyl)-4,6-androstadien-3-one is obtained. One gram of the thus-produced 17β-acetoxy-17α-(3-hydroxypropyl)-4,6-androstadien-3-one is refluxed for one hour in 5 ml. of methanol and 0.5 ml. of thioacetic acid. After evaporation under vacuum and crystallization from acetone-hexane, 17β-acetoxy-17α-(3-hydroxypropyl)-7α-acetylthio-4-androsten-3-one is obtained, m.p. 135°–140° C.

EXAMPLE 52

4 g. of 17β-hydroxy-17α-(3-hydroxypropyl)-4,6-estradien-3-one is reacted as described in Example 51 in 10 ml. of pyridine with 5 ml. of acetic anhydride to obtain 17β-acetoxy-17α-(3-acetoxypropyl)-4,6-estradien-3-one. One gram of the thus-produced diacetate is dissolved in 5 ml. of methanol and 5 ml. of methylene chloride, cooled to 0° C., and stirred with a solution of 0.6 g. of potassium hydroxide in 2 ml. of methanol for 60 minutes at 20° C. under argon. After neutralization with acetic acid, the reaction mixture is evaporated and worked up. Purification by chromatography yields 0.8 g. of 17β-acetoxy-17α-(3-hydroxypropyl)-4,6-estradien-3-one. In 3 ml. of methanol, 0.5 g. of the thus-produced 17β-acetoxy-17α-(3-hydroxypropyl)-4,6-estradien-3-one is reacted with 0.5 ml. of thioacetic acid. After the mixture has been worked up and purified, 17β-acetoxy- 17α-(3-hydroxypropyl)-7α-acetylthio-4-estren-3-one is obtained.

EXAMPLE 53

1.5 g. of 17β-hydroxy-17α-(3-hydroxypropyl)-4,6-androstadien-3-one is dissolved in 5 ml. of pyridine, 1.5 g. of succinic anhydride is added thereto, and the mixture is heated to boiling under argon gas for 1 hour. After cooling, the mixture is stirred into ice water, acidified with hydrochloric acid, and extracted with ethyl acetate. The ethyl acetate extract is washed neutral with water, dried over sodium sulfate, and evaporated under vacuum, thus obtaining 2 g. of amorphous 17β-hydroxy-17α-(3-hydroxysuccinyloxypropyl)-4,6-androstadien-3-one.

UV: $\epsilon_{285} = 23,700$.

EXAMPLE 54

300 mg. of the hemisuccinate produced in Example 53 is dissolved in 15 ml. of absolute methanol and adjusted to pH 8 with 0.1-normal sodium methylate solution (5.5 ml.). The solution is concentrated under vacuum and precipitated into 200 ml. of ether. The thus-precipitated sodium salt is vacuum-filtered, dissolved in methanol, and again precipitated into ether, thus obtaining 210 mg. of 17β-hydroxy-17α-(3-hydroxysuccinyloxypropyl)-4,6-androstadien-3-one sodium salt, m.p. 120° C. (decomposition).

UV: $\epsilon_{285} = 24,100$.

EXAMPLE 55

400 mg. of the hemisuccinate prepared in Example 53 is adjusted to pH 8 in 20 ml. of absolute methanol with 5.4 ml. of 0.1-normal potassium methylate solution. After reprecipitation in ether as described in Example 54, 285 mg. of 17β-hydroxy-17α-(3-hydroxysuccinyloxypropyl)-4,6-androstadien-3-one potassium salt, m.p. 145° C. (decomposition), is obtained.

EXAMPLE 56

Analogously to Example 53, by esterification with glutaric acid anhydride in pyridine and subsequent reaction with potassium methylate analogously to Example 55, 17β-hydroxy-17α-(3-hydroxyglutaryloxypropyl)-4,6-androstadien-3-one potassium salt is obtained, m.p. 98° C. (decomposition).

EXAMPLE 57

A solution of 1 g. of 17β-hydroxy-17α-(3-hydroxypropyl)-4,6-estradien-3-one in 4 ml. of pyridine is heated to boiling for one hour under argon with 1 g. of succinic anhydride. The reaction mixture is allowed to cool and stirred into ice water, then acidified with dilute hydrochloric acid, and extracted with ethyl acetate. The combined extracts are washed with water, dried over sodium sulfate, and evaporated to dryness, thus obtaining 1 g. of crude 17β-hydroxy-17α-(3-hydroxysuccinyloxypropyl)-4,6-estradien-3-one as an amorphous substance.

UV: $\epsilon_{284} = 26,800$ (methanol).

EXAMPLE 58

A solution of 500 mg. of 17β-hydroxy-17α-(3-hydroxysuccinyloxypropyl)-4,6-estradien-3-one in 15 ml. of absolute methanol is adjusted to pH 8 with the use of a pH meter with 0.1-normal sodium methylate solution, concentrated under vacuum, and precipitated in 200 ml. of ether. The sodium salt is vacuum-filtered, dissolved in methanol, and again precipitated with eth ., thus obtaining 350 mg. of 17β-hydroxy-17α-(3-hydroxysuccinyloxypropyl)-4,6-estradien-3-one as the sodium salt.

UV: $\epsilon_{285} = 25,900$ (methanol).

EXAMPLE 59

A solution of 600 mg. of 17β-hydroxy-17α-(3-hydroxysuccinyloxypropyl)-4,6-estradien-3-one in 30 ml. of absolute methanol is adjusted to pH 8 with 0.1-normal potassium methylate solution. After reprecipitation in ether, as described in Example 54, 320 mg. of the potassium salt of 17β-hydroxy-17α-(3-hydroxysuccinyloxypropyl)-4,6-estradien-3-one is obtained.

UV: $\epsilon_{284} = 26,300$ (methanol).

EXAMPLE 60

As described in Example 57, by esterification of 17β-hydroxy-17α-(3-hydroxypropyl)-4,6-estradien-3-one with glutaric acid anhydride in pyridine and subsequent reaction with potassium methylate, 17β-hydroxy-17α-(3-hydroxy-glutaryloxypropyl)-4,6-estradien-3-one is produced as the potassium salt.

EXAMPLE 61

55 g. of 17β-hydroxy-17α-(3-hydroxypropyl)-4,6-androstadien-3-one is heated in 350 ml. of pyridine with 70 g. of triphenylmethyl chloride for 40 minutes on a steam bath. The reaction mixture is cooled, gradually stirred into 8 l. of ice water, and the thus-precipitated product is vacuum-filtered, washed with water, and dried. The crude product is chromatographed on silica gel and recrystallized from ether-pentane, thus producing 61.4 g. of 17β-hydroxy-17α-(3-triphenylmethoxypropyl)-4,6-androstadien-3-one, m.p. 168°–169° C.

EXAMPLE 62

27 g. of trimethylsulfoxonium iodide and 4.6 g. of 55% sodium hydride dispersion in oil are stirred in 500 ml. of dimethyl sulfoxide for 1.5 hours under argon gas. Thereafter, 55 g. of 17β-hydroxy-17α-(3-triphenylmethoxypropyl)-4,6-androstadien-3-one is introduced and the mixture is agitated for 24 hours at room temperature. Subsequently, the mixture is combined with water, extracted with ethyl acetate, and the separated ethyl acetate solution is washed with water and evaporated. The residue is chromatographed on silica gel. By elution with hexane-ethyl acetate, 26.5 g. of 6,7-methylene adduct is obtained which is composed of 70% β-methylene and 30% α-methylene compound.

For ether cleavage, 26.5 g. of the 6,7-methylene compound is dissolved in 170 ml. of 80% acetic acid and heated for 15 minutes on a steam bath. The solution is then poured into ice water. The thus-precipitated product is vacuum-filtered, dried, and recrystallized from acetone-hexane, thus obtaining 10 g. of 17β-hydroxy-17α-(3-hydroxypropyl)-6β,7β-methylene-4-androsten-3-one, m.p. 182°–184° C.

UV: $\epsilon_{266} = 18,800$.

By chromatography of the mother liquors and repeated recrystallization from acetone-hexane, 1.2 g. of 17β-hydroxy-17α-(3-hydroxypropyl)-6α,7α-methylene-4-androsten-3-one is obtained, m.p. 191°–192° C.

UV: $\epsilon_{260} = 17,000$.

EXAMPLE 63

3 g. of 17α-(3-hydroxypropyl)-17β-hydroxy-4,6-androstadien-3-one is suspended in 15 ml. of acetone and 6 ml. of methanol, combined with 1.29 ml. of thioacetic acid, and heated to boiling for 45 minutes. The reaction mixture is worked up, after termination of the reaction, analogously to Example 1, thus obtaining 2.4 g. of 17α-(3-hydroxypropyl)-17β-hydroxy-7α-thioacetyl-4-androsten-3-one, m.p. 187°-192° C.

UV: ε$_{239}$ = 18,400.

EXAMPLE 64

0.5 g. of 17β-(3-hydroxypropyl)-17β-hydroxy-4,6-androstadien-3-one is suspended in 2.5 ml. of tetrahydrofuran and 1 ml. of methanol and combined with 0.22 ml. of thioacetic acid. After heating the mixture under reflux for one hour, the mixture is worked up analogously to Example 1, thus obtaining 0.34 g. of 17α-(3-hydroxypropyl)-17β-hydroxy-7α-thioacetyl-4-androsten-3-one, m.p. 187°-192° C.

UV: ε$_{239}$ = 18,400.

EXAMPLE 65

1.5 g. of 17β-hydroxy-17α-(3-hydroxypropyl)-6β,7β-methylene-4-androsten-3-one is combined in 5 ml. of pyridine with 1.5 ml. of acetic anhydride and stirred for 105 minutes at 22° C. After the mixture has been worked up and triturated with hexane, 1.7 g. of amorphous 17β-hydroxy-17α-(3-acetylpropyl)-6β,7β-methylene-4-androsten-3-one is obtained.

EXAMPLE 66

500 mg. of 17β-hydroxy-17α-(3-hydroxypropyl)-4,6-androstadien-3-one is combined in 15 ml. of diethyl carbonate with 10 mg. of sodium methylate and heated under agitation and argon gas for 10 minutes to 140° C. The mixture is then cooled, neutralized with acetic acid, and evaporated under vacuum. After purification by layer chromatography, 400 mg. of 17β-hydroxy-17α-(3-ethoxycarbonyloxypropyl)-4,6-androstadien-3-one is obtained as a colorless oil.

UV: ε$_{285}$ = 26,100.

EXAMPLE 67

300 mg. of the ethyl carbonate produced in Example 66 is heated under reflux in 3 ml. of methanol and 0.3 ml. of thioacetic acid for one hour under argon. After evaporation under vacuum and layer chromatography in the system ether/pentane (75:25), 210 mg. of 17β-hydroxy-17α-(3-ethoxycarbonyloxypropyl)-7α-acetylthio-4-androsten-3-one is obtained.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

In addition to the compounds of the preceding Examples, the following are additional illustrative compounds of the invention: Ethyl ester of 17β-hydroxy-17α-(3-acetyloxypropyl)-3-oxo-4-androsten-7α-carboxylic acid and Ethyl ester of 17β-hydroxy-17α-(acetyloxypropyl)-6α-methyl-3-oxo-4-androsten-7α-carboxylic acid.

What is claimed is:

1. A 4-androsten-3-one of the formula

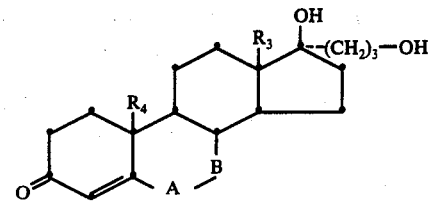

wherein
R$_3$ is methyl or ethyl,
R$_4$ is hydrogen or methyl,

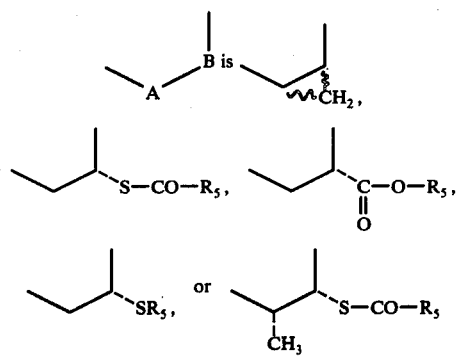

R$_5$ is alkyl or up to 5 carbon atoms, or a physiologically acceptable (a) 17β-hydroxy mono ester thereof, or (b) 17α-(3-hydroxypropyl) mono ester thereof or mono ether thereof, (c) 17β-hydroxy mono ester, 17α-(3-hydroxypropyl) mono ether thereof, or (d) 17β-hydroxy-17α-(3-hydroxypropyl) diester thereof.

2. 17β-Hydroxy-17α-(3-hydroxypropyl)-7α-thioacetyl-4-androsten-3-one, a compound of claim 1.

3. Ethyl ester of 17β-nitryloxy-17α-(3-nitryloxypropyl)-3-oxo-4-androstene-7α-carboxylic acid, a compound of claim 1.

4. Ethyl ester of 17β-hydroxy-17α-(3-hydroxypropyl)-3-oxo-4-androstene-7α-carboxylic acid, a compound of claim 1.

5. Methyl ester of 17β-nitryloxy-17α-(3-nitryloxypropyl)-3-oxo-4-androstene-7α-carboxylic acid, a compound of claim 1.

6. Methyl ester of 17β-hydroxy-17α-(3-hydroxypropyl)-3-oxo-4-androstene-7α-carboxylic acid, a compound of claim 1.

7. 17β-Hydroxy-17α-(3-ethoxyacetoxypropyl)-7α-acetylthio-4-androsten-3-one, a compound of claim 1.

8. 17β-Hydroxy-17α-(3-hydroxypropyl)-7α-propionylthio-4-androsten-3-one, a compound of claim 1.

9. 17β-Hydroxy-17α-(3-hydroxypropyl)-6β,7β-methylene-4-androsten-3-one, a compound of claim 1.

10. 17β-Nitryloxy-17α-(3-nitryloxypropyl)-7α-thioacetyl-4-androsten-3-one, a compound of claim 1.

11. 7α-Acetylthio-17β-hydroxy-17α-(3-hydroxypropyl)-18-methyl-4-estren-3-one, a compound of claim 1.

12. 17β-Hydroxy-17α-(3-hydroxypropyl)-18-methyl-7α-propionylthio-4-estren-3-one, a compound of claim 1.

13. 17β-Hydroxy-17α-(3-hydroxypropyl)-18-methyl-6β,7β-methylene-4-estren-3-one, a compound of claim 1.

14. 7α-Acetylthio-17β-hydroxy-18-methyl-17α-(3-propionyloxyacetoxypropyl)-4-estren-3-one, a compound of claim 1.

15. 17β-Hydroxy-17α-(3-acetoxyacetyloxypropyl)-18-methyl-6β,7β-methylene-4-estren-3one, a compound of claim 1.

16. 7α-Acetylthio-17β-hydroxy-17α-(3-acetoxypropyl)-18-methyl-4-estren-3-one, a compound of claim 1.

17. 17β-Hydroxy-17α-(3-acetoxypropyl)-18-methyl-6β,7β-methylene-4-estren-3-one, a compound of claim 1.

18. 7α-Acetylthio-17β-hydroxy-17α-(3-methoxypropyl)-18-methyl-4-estren-3-one, a compound of claim 1.

19. 7α-Acetylthio-17β-hydroxy-18-methyl-17α-(3-triphenylmethoxypropyl)-4-estren-3-one, a compound of claim 1.

20. 7α-Acetylthio-17β-hydroxy-17α-(3-hydroxypropyl)-4-estren-3-one, a compound of claim 1.

21. 17β-Hydroxy-17α-(3-hydroxypropyl)-7α-propionylthio-4-estren-3-one, a compound of claim 1.

22. 17β-Hydroxy-17α-(3-hydroxypropyl)-6β,7β-methylene-4-estren-3-one, a compound of claim 1.

23. 7α-Acetylthio-17β-hydroxy-17α-(3-propionyloxyacetyloxypropyl)-4-estren-3-one, a compound of claim 1.

24. 17β-Hydroxy-17α-(3-acetoxyacetyloxypropyl)-6β,7β-methylene-4-estren-3-one, a compound of claim 1.

25. 7α-Acetylthio-17β-hydroxy-17α-(3-acetoxypropyl)-4-estren-3-one, a compound of claim 1.

26. 17β-Hydroxy-17α-(3-acetoxypropyl)-6β,7β-methylene-4-estren-3-one, a compound of claim 1.

27. 7α-Acetylthio-17β-hydroxy-17α-(3-methoxypropyl)-4-estren-3-one, a compound of claim 1.

28. 7α-Acetylthio-17β-hydroxy-17α-(3-triphenylmethoxypropyl)-4-estren-3-one, a compound of claim 1.

29. 17β-Hydroxy-17α-(3-hydroxypropyl)-7α-ethylthio-4-androsten-3-one, a compound of claim 1.

30. 17β-Hydroxy-17α-(3-hydroxypropyl)-7α-butylthio-4-androsten-3-one, a compound of claim 1.

31. 17β-Acetoxy-17α-(3-acetoxypropyl)-7α-thioacetyl-4-androsten-3-one, a compound of claim 1.

32. 17β-Hydroxy-17α-(3-propionyloxypropyl)-7α-propionylthio-4-androsten-3-one, a compound of claim 1.

33. 17β-Acetoxy-17α-(3-propionyloxypropyl)-7α-propionylthio-4-androsten-3-one, a compound of claim 1.

34. 17β-Hydroxy-17α-(3-acetoxypropyl)-7α-acetylthio-4-androsten-3-one, a compound of claim 1.

35. 17β-Acetoxy-17α-(3-acetoxypropyl)-7α-acetylthio-4-androsten-3-one, a compound of claim 1.

36. 17β-Acetoxy-17α-(3-acetoxypropyl)-6β,7β-methylene-4-androsten-3-one, a compound of claim 1.

37. 17β-Acetoxy-17α-(3-acetoxypropyl)-7α-thioacetyl-4-estren-3-one, a compound of claim 1.

38. 17β-Hydroxy-17α-(3-propionyloxypropyl)-7α-propionylthio-4-estren-3-one, a compound of claim 1.

39. 17β-Acetoxy-17α-(3-propionyloxypropyl)-7α-propionylthio-4-estren-3-one, a compound of claim 1.

40. 17β-Hydroxy-17α-(3-undecyloxypropyl)-7α-thioacetyl-4-androsten-3-one, a compound of claim 1.

41. 17β-Acetoxy-17α-(3-hydroxypropyl)-7α-acetylthio-4-androsten-3-one, a compound of claim 1.

42. 17β-Acetoxy-17α-(3-hydroxypropyl)-7α-acetylthio-4-estren-3-one, a compound of claim 1.

43. 17β-Hydroxy-17α-(3-acetoxypropyl)-6α-methyl-7α-acetylthio-4-androsten-3-one, a compound of claim 1.

44. 17β-Hydroxy-17α-(3-hydroxypropyl)-7α-acetylthio-6α-methyl-4-androsten-3-one, a compound of claim 1.

45. 17β-Hydroxy-17α-(3-butyryloxypropyl)-7α-acetylthio-6α-methyl-4-androsten-3-one, a compound of claim 1.

46. 17β-Hydroxy-17α-(3-hydroxypropyl)-7α-propionylthio-6α-methyl-4-androsten-3-one, a compound of claim 1.

47. 17β-Hydroxy-17α-(3-hemisuccinyloxypropyl)-6-methyl-4,6-androstadien-3-one, a compound of claim 1.

48. 17β-Hydroxy-17α-(3-hemisuccinyloxypropyl)-6-methyl-4,6-androstadien-3-one potassium salt, a compound of claim 1.

49. 17β-Hydroxy-17α-(3-hemisuccinyloxypropyl)-6-methyl-4,6-androstadien-3-one sodium salt, a compound of claim 1.

50. 7α-Acetylthio-17β-hydroxy-17α-(3-hydroxy-succinyloxypropyl)-4-estren-3-one, a compound of claim 1.

51. 7α-Acetylthio-17β-hydroxy-17α-(3-hydroxysuccinyloxypropyl)-4-estren-3-one potassium salt, a compound of claim 1.

52. 17β-Hydroxy-17α-(3-hydroxypropyl)-7α-ethylthio-4-estren-3-one, a compound of claim 1.

53. 17β-Hydroxy-17α-(3-hydroxypropyl)-18-methyl-7α-ethylthio-4-estren-3-one, a compound of claim 1.

54. 17β-Hydroxy-17α-(3-hydroxysuccinyloxypropyl)-7α-acetylthio-4-androsten-3-one.

55. 17β-Hydroxy-17α-(3-hydroxysuccinyloxypropyl)-7α-acetylthio-4-androsten-3-one potassium salt.

56. 17β-Hydroxy-17α-(3-hydroxypropyl)-6α,7α-methylene-4-androsten-3-one, a compound of claim 1.

57. 17β-Hydroxy-17α-(3-acetylpropyl)-6β,7β-methylene-4-androsten-3-one, a compound of claim 1.

58. 17β-Hydroxy-17α-(3-ethoxycarbonyloxypropyl)-7α-acetylthio-4-androsten-3-one, a compound of claim 1.

59. A pharmaceutical composition comprising, in unit dosage form, a diuretically effective amount per unit dosage of a compound of claim 1, in admixture with a pharmaceutically acceptable carrier.

60. A pharmaceutical composition comprising, in unit dosage form, and in admixture with a pharmaceutically acceptable carrier, a diuretically effective amount per unit dosage of a 4,6-androstadiene-3-one of the formula

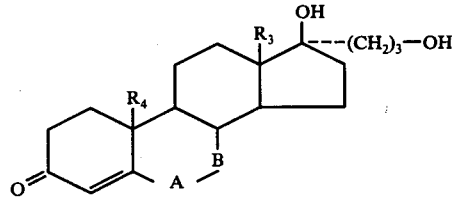

wherein $R_3$ is methyl or ethyl, $R_4$ is hydrogen or methyl,

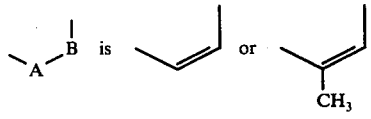

or a physiologically acceptable (a) 17β-hydroxy mono ester thereof, or (b) 17α-(3-hydroxypropyl) mono ester thereof or mono ether thereof, (c) 17β-hydroxy mono ester, 17α-(3-hydroxypropyl) mono ether thereof, or (d) 17β-hydroxy-17α-(3-hydroxypropyl) diester thereof.

61. A composition of claim 60 wherein the 4,6-androstadiene-3-one is 17β-hydroxy-17α-(3-hydroxypropyl)-6-methyl-4,6-androstadien-3-one.

62. A composition of claim 60 wherein the 4,6-androstadiene-3-one is 17β-hydroxy-17α-(3-hydroxysuccinyloxypropyl)-4,6-androstadien-3-one.

63. A composition of claim 60 wherein the 4,6-androstadiene-3-one is 17β-hydroxy-17α-(3-hydroxysuccinyloxypropyl)-4,6-androstadien-3-one sodium salt.

64. A composition of claim 60 wherein the 4,6-androstadiene-3-one is 17β-hydroxy-17α-(3-hydroxysuccinyloxypropyl)-4,6-androstadien-3-one potassium salt.

65. A composition of claim 60 wherein the 4,6-androstadiene-3-one is 17β-hydroxy-17α-(3-hydroxyglutaryloxypropyl)-4,6-androstadien-3-one potassium salt.

66. A composition of claim 60 wherein the 4,6-androstadiene-3-one is 17β-hydroxy-17α-(3-hydroxysuccinyloxypropyl)-4,6-estradien-3-one.

67. A composition of claim 60 wherein the 4,6-androstadiene-3-one is 17β-hydroxy-17α-(3-hydroxysuccinyloxypropyl)-4,6-estradien-3-one sodium salt.

68. A composition of claim 60 wherein the 4,6-androstadiene-3-one is 17β-hydroxy-17α-(3-hydroxysuccinyloxypropyl)-4,6-estradien-3-one potassium salt.

69. A composition of claim 60 wherein the 4,6-androstadiene-3-one is 17β-hydroxy-17α-(3-hydroxyglutaryloxypropyl)-4,6-estradien-3-one potassium salt.

70. A composition of claim 60 wherein the 4,6-androstadiene-3-one is 17β-hydroxy-17α-(3-hydroxysuccinyloxypropyl)-18-methyl-4,6-estradien-3-one.

71. A composition of claim 60 wherein the 4,6-androstadiene-3-one is 17β-hydroxy-17α-(3-hydroxysuccinyloxypropyl)-18-methyl-4,6-estradien-3-one potassium salt.

72. A composition of claim 60 wherein the 4,6-androstadiene-3-one is 17β-hydroxy-17α-(3-ethoxycarbonyloxypropyl)-4,6-androstadien-3-one.

73. A method of inducing diuresis in a human patient which comprises administering thereto a diuretically effective amount of claim 1.

74. A method of inducing diuresis in a human patient which comprises administering thereto a unit dosage amount of a pharmaceutical composition of claim 60.

* * * * *